(12) United States Patent
Redmond

(10) Patent No.: US 6,783,030 B2
(45) Date of Patent: Aug. 31, 2004

(54) EASY OPENING SEALED CONTAINMENT AND DISPENSING PACKAGE

(76) Inventor: Sanford Redmond, 746 Riverbank Rd., Stamford, CT (US) 09603

( * ) Notice: Subject to any disclaimer, the term of this patent is extended or adjusted under 35 U.S.C. 154(b) by 0 days.

(21) Appl. No.: 10/189,399

(22) Filed: Jul. 8, 2002

(65) Prior Publication Data

US 2002/0195461 A1 Dec. 26, 2002

Related U.S. Application Data

(63) Continuation-in-part of application No. 09/717,449, filed on Nov. 20, 2000, now Pat. No. 6,415,939.
(60) Provisional application No. 60/166,504, filed on Nov. 19, 1999, provisional application No. 60/184,512, filed on Feb. 24, 2000, provisional application No. 60/185,779, filed on Feb. 29, 2000, provisional application No. 60/211,865, filed on Jun. 14, 2000, provisional application No. 60/212,977, filed on Jun. 21, 2000, provisional application No. 60/224,654, filed on Aug. 11, 2000, and provisional application No. 60/228,434, filed on Aug. 28, 2000.

(51) Int. Cl.[7] .............................................. B65D 35/08

(52) U.S. Cl. ....................................................... 222/107

(58) Field of Search ........................... 222/107; 383/66, 383/203

(56) References Cited

U.S. PATENT DOCUMENTS

| | | | |
|---|---|---|---|
| 2,226,049 A | | 12/1940 | Carley |
| 2,390,822 A | | 12/1945 | Wren |
| 2,397,051 A | | 3/1946 | Scherer |
| 3,127,085 A | | 3/1964 | Hill |
| 3,182,861 A | * | 5/1965 | Nafaf .......................... 222/212 |
| 3,453,661 A | | 7/1969 | Repko |
| 3,788,549 A | | 1/1974 | Ostrowsky |
| 3,913,734 A | * | 10/1975 | Siegel ......................... 206/470 |
| 4,139,665 A | * | 2/1979 | Herrero ....................... 428/36.7 |
| 4,420,080 A | | 12/1983 | Nakamura |
| 4,640,425 A | | 2/1987 | Cabernoch |
| 4,770,325 A | | 9/1988 | Gordon et al. |

(List continued on next page.)

FOREIGN PATENT DOCUMENTS

| | | |
|---|---|---|
| DE | 75 33 999 | 5/1977 |
| DE | 93 06 584 | 6/1993 |
| EP | 0 322 980 | 7/1989 |
| GB | 1 592 560 | 7/1981 |
| WO | WO 97/27043 | 7/1997 |
| WO | WO 01/36293 A1 | 5/2001 |

OTHER PUBLICATIONS

Pliant Corp. "Barrier Film Product Guide" (page listing Unilock 242, Unipeel 353, Unipeel 445, Unilon 9006, Uinion 9767).

*Primary Examiner*—Philippe Derakshani
(74) *Attorney, Agent, or Firm*—Kenyon & Kenyon

(57) ABSTRACT

A pouch style containment and dispensing package for flowable products is provided. The package comprises at least three layers of thin materials selected from a group of materials including heat sealable plastic films, metal foils, oxygen barrier films, plastic moisture barrier films, adhesives, coextrudable plastics and high strength plastics. The package includes an aperture or aperture forming means and a flap portion that is folded over and sealed to cover the aperture or aperture forming means, so that when the flap portion is folded back and away, an aperture is exposed or created. The layers may be selected so that a contact face of the flap member is sealed at a lower temperature than a sealing temperature for forming edge seals on the inner product contacting wall layers. Also, one layer may comprise a high strength layer that will not lose a significant amount of strength at temperatures substantially higher than the edge sealing temperature. Also, the invention provides a pouch style package having a pre-formed bulge in at least one wall to increase its product containment capability.

20 Claims, 2 Drawing Sheets

U.S. PATENT DOCUMENTS

| | | | |
|---|---|---|---|
| 4,836,384 A | | 6/1989 | Tuns et al. |
| 4,967,910 A | | 11/1990 | Schuster |
| 5,203,379 A | * | 4/1993 | Holoubek et al. .......... 138/109 |
| 5,307,955 A | * | 5/1994 | Viegas ........................ 222/107 |
| 5,779,110 A | | 7/1998 | Brown et al. |
| 5,826,737 A | | 10/1998 | Zakensberg |
| 5,975,359 A | * | 11/1999 | Van Marcke ................. 222/82 |
| 6,062,413 A | | 5/2000 | Redmond |
| 6,085,941 A | | 7/2000 | Pauser et al. |
| 6,244,467 B1 | | 6/2001 | Lewit |
| 6,415,939 B1 | | 7/2002 | Redmond |
| 2001/0030192 A1 | | 10/2001 | Redmond |

* cited by examiner

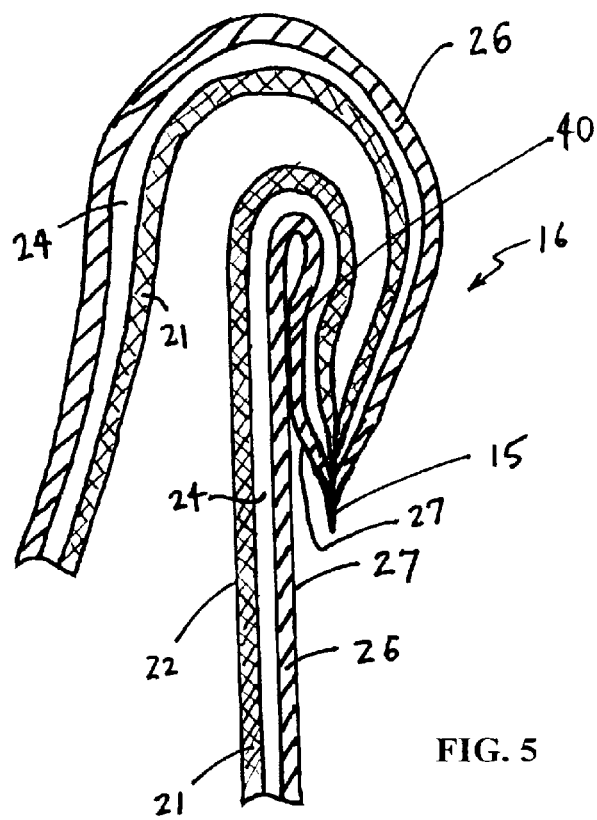
FIG. 5
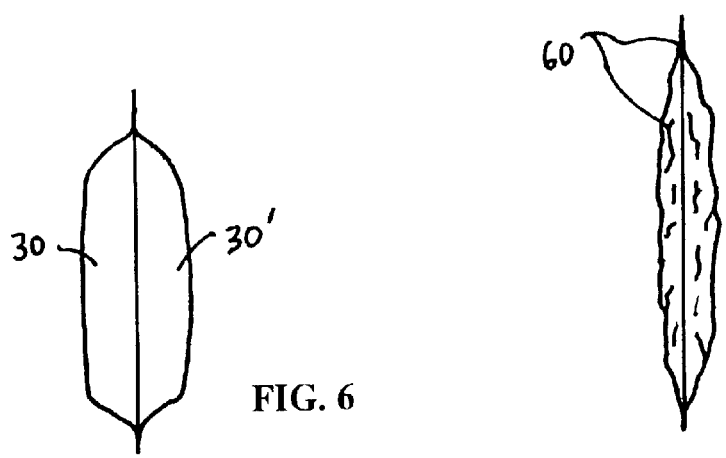
FIG. 6
FIG. 7
PRIOR ART

EASY OPENING SEALED CONTAINMENT AND DISPENSING PACKAGE

RELATED APPLICATIONS

This application is a continuation-in-part (CIP) of U.S. application Ser. No. 09/717,449, filed Nov. 20, 2000 now U.S. Pat. No. 6,415,939, entitled "RECLOSABLE DISPENSER PACKAGE, RECLOSABLE OUTLET FORMING STRUCTURE AND METHOD AND APPARATUS FOR MAKING SAME", the disclosure of which is hereby incorporated by reference herein. This application and U.S. application Ser. No. 09/717,449 also claim priority to U.S. Provisional Application Ser. No. 60/166,504, filed Nov. 19, 1999, entitled "RECLOSABLE DISPENSER PACKAGE, RECLOSABLE OUTLET FORMING STRUCTURE AND METHOD AND APPARATUS FOR MAKING SAME", U.S. Provisional Application Ser. No. 60/184,512, filed Feb. 24, 2000, entitled "RECLOSABLE DISPENSER PACKAGE, RECLOSABLE OUTLET FORMING STRUCTURE AND METHOD AND APPARATUS FOR MAKING SAME", U.S. Provisional Application Ser. No. 60/185,779, filed Feb. 29, 2000, entitled "RECLOSABLE DISPENSER PACKAGE, RECLOSABLE OUTLET FORMING STRUCTURE AND METHOD AND APPARATUS FOR MAKING SAME", U.S. Provisional Application Ser. No. 60/211,865, filed Jun. 14, 2000, entitled "EASY OPENING POUCH", U.S. Provisional Application Ser. No. 60/212,977, filed Jun. 21, 2000, entitled "EASY OPENING POUCH", U.S. Provisional Application Ser. No. 60/224,654, filed Aug. 11, 2000, entitled "EASY OPENING POUCH", and U.S. Provisional Application Ser. No. 60/228,434, filed Aug. 28, 2000, entitled "EASY OPENING POUCH", all by the same inventor of the instant non-provisional application, and all of which are hereby incorporated by reference herein.

FIELD OF THE INVENTION

The invention relates to easy opening, self-contained, easy to use dispenser packages capable of economical, high-speed production, manufactured from a broad range of materials, many of which are recyclable.

BACKGROUND OF THE INVENTION

The universal use of pouch style packages for a broad spectrum of products ranging from ketchup and other condiments to health and beauty aids as well as medical products in addition to various other foods and technical products is well known. Until the present they have been made of foil/plastic laminates. The underlying invention of the parent application is a pouch that instantly opens when the flap is raised. In a preferred embodiment it may be made of coextruded plastics comprised of as many as seven layers with a total thickness of about 0.0025" to 0.003". These layers typically must have very specific properties including oxygen barriers, moisture barriers, varying sealing and/or softening temperatures and printable surfaces. These films are typically delivered in large diameter rolls.

It has been further unexpectedly discovered that the walls of these pouches, even those containing a layer of foil all within the total thickness of about 0.0025" to 0.003" can be made with preformed bulges thus lowering costs in the range of about 20% to 30%. As an ancillary benefit the bulges eliminate wrinkles in the walls of the pouches.

SUMMARY OF THE INVENTION

This application is a continuation-in-part (CIP) of my earlier U.S. application Ser. No. 09/717,449, filed Nov. 20, 2000, entitled "RECLOSABLE DISPENSER PACKAGE, RECLOSABLE OUTLET FORMING STRUCTURE AND METHOD AND APPARATUS FOR MAKING SAME", in which I claim an easy opening pouch or other type containment package wherein a flap member, either integral to the package or independently made and integrated with the package, is folded or hinged over and sealingly attached to cover one of a number of apertures or aperture forming structures, e.g., a hole, a cut pattern, a breakaway tip and/or a score pattern, whereby raising said flap member creates or uncovers an aperture in the wall of the containment package.

One of the major problems in the development of the coextrusions of plastic for the subject pouches is that the flap, when folded over and sealed to the outer surface of the pouch, needs to be sealed without inadvertently sealing together the inner surfaces of the pouch. If the inner surfaces are inadvertently sealed together at the wrong locations they could obstruct the outflow of the product. (As disclosed in U.S. application Ser. No. 09/717,449, where desired, highly controlled and precisely located seal patterns that selectively seal together portions of the inner surfaces of the pouch can be used to create a specific flow path inside of the pouch to control the rate of flow from the outlet of the contained product and to act as a valve.)

In accordance with certain embodiments of the invention, the flap surface layer which folds over and seals to the outer surface of the pouch is made of a material which seals at a significantly lower temperature than the plastic film layer of the inner wall surfaces which must be sealed together to create the edge seals. This avoids inadvertent sealing together of the inner wall surfaces when the flap surface layer is folded over and sealed.

In accordance with further embodiments of the invention, a third component layer of the multilayer film is provided which will not lose strength at substantially higher temperatures than the sealing temperatures used to seal together the inner wall surfaces of the plastic film layer to create the edge seals. This is necessary because the film of the pouches must retain its tensile strength in order to be pulled through the machine that makes the pouches, generally by draw-rollers. This tension force is significant, particularly on the cross edge seals which are at right angles (90°) to the direction of draw. If the seals are weakened or softened while still at the edge sealing temperature, they would stretch and/or pull apart, and the machine could not function properly.

Referring now specifically to the pouch style packages claimed in my underlying U.S. application Ser. No. 09/717,449, in these easy opening pouches, the flap member should not contain any product. This is because product in the flap member could adversely affect the ability of the flap to seal to the outer surface of the pouch, because the product in the flap could cool the film of the flap, thereby not allowing heat to seal it. Thus, the fill level of the pouch should be below the lowest line of the flap. In addition, in those versions where the flap covers a hole or cut pattern, the product, if filled too high, could or would flow or spill out of the hole or cut pattern and contaminate the flap seal. Old style foil based packages not having such a flap do not have this restriction and are generally shorter than the easy opening pouches of U.S. application Ser. No. 09/717,449.

Although the material cost of the all-plastic versions the pouches of U.S. application Ser. No. 09/717,449 is significantly lower than the cost of the foil based old style packages, if the material cost differential from the old style packages could be increased it would be a great improvement. In addition it is axiomatic that all pouches made of flat material must wrinkle when being made simply because they have flat edge seals yet the containment walls must be contoured to encompass the product contained; curved surfaces intersecting with flat surfaces must create wrinkles. It occurred to me that if I could pre-form a bulge pocket formation in the containment walls I could eliminate the wrinkles and reduce the overall material required to contain the same amount of product, thereby greatly reducing the cost of the pouch. I had, however, doubts about forming such thin film of about two and a half thousandths of an inch in thickness (0.0025"–0.003"). I ran some tests and got very unexpected results. I was able to form a bulge in a wall without overly reducing the wall thickness (and therefore without overly reducing barrier qualities). Actually, packages in accordance with this invention have been produced with such bulges in one side only that have resulted in increasing the volume contained by as much as 40% and bringing the material cost down so low that it costs only about ⅓ that of an old style pouch made with a foil layer.

On another subject, as previously mentioned, the wide use of aluminum foil/plastic laminates for the production of old style pouch packages with no flap for a broad spectrum of products ranging from ketchup and other condiments to health and beauty aids as well as medical products, and all sorts of other food and technical products, such as glues, epoxies, etc., etc., is well known. They are generally made of combinations of very thin layers laminated together to an overall thickness total of about 0.003" (three thousands of an inch). These materials are made into rolls of flat material. These rolls of flat material are then mounted on high-speed pouch making machines, which are utilized to produce the pouches. Since pouches are not flat, it is necessary that they wrinkle at the seals and various of their other surfaces, and it has been generally assumed that these very thin aluminum foil layers used in the laminations generally of a thickness of two to three ten thousandths of an inch (0.0002"–0.0003") cannot be formed without rupturing. It has been unexpectedly discovered that the material used to form these aluminum foil based pouches does allow for some minimum forming and can be formed with slightly bulging formations, on at least one and in some cases both of their side walls. These formations allow for significantly greater containment volume and tend to eliminate seal wrinkles, since, as above-mentioned, the aluminum does stretch to a slight degree. This additionally means that there can be significantly less material used to contain the same quantity of product even in these aluminum foil based pouches, in the range of ten (10) to thirty (30) percent.

It will be appreciated by those skilled in the art that the forgoing various brief descriptions and the following detailed descriptions are exemplary and explanatory of the present invention, but are not intended to be restrictive thereof or limiting of the advantages which can be achieved by the invention or various combinations thereof. The accompanying drawings, referred to herein and constituting a part hereof, illustrate preferred embodiments of the invention and, together with the detailed description, serve to explain the principles of the invention.

BRIEF DESCRIPTION OF THE DRAWINGS

FIG. 5 is a cross-sectional view showing edge and flap seals in accordance with certain embodiments of the present invention.

FIG. 6 is a side view of a foil pouch style package with two-sided bulged in accordance with certain embodiments of the present invention.

FIG. 7 is a side view of a PRIOR ART foil pouch.

DETAILED DESCRIPTION OF THE INVENTION

Figure 1:
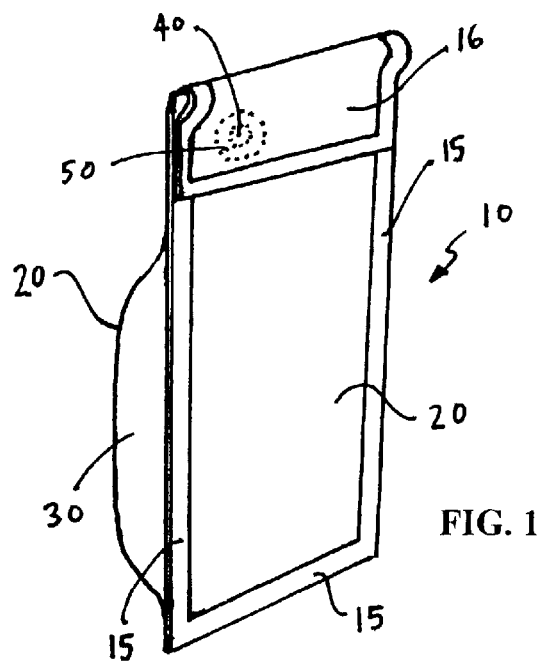
FIG. 1 is a front perspective view of the pouch style package in accordance with one embodiment of the present invention.

Referring now to the accompanying drawings, where like reference numerals depict like elements, preferred embodiments of the present invention will be discussed below.

Figure 2:
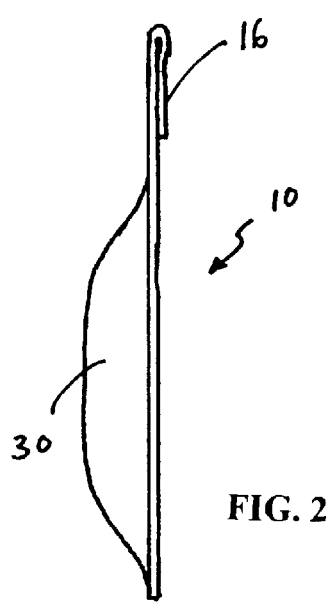
FIG. 2 is a side view of the pouch style package shown in FIG. 1.
Figure 4:
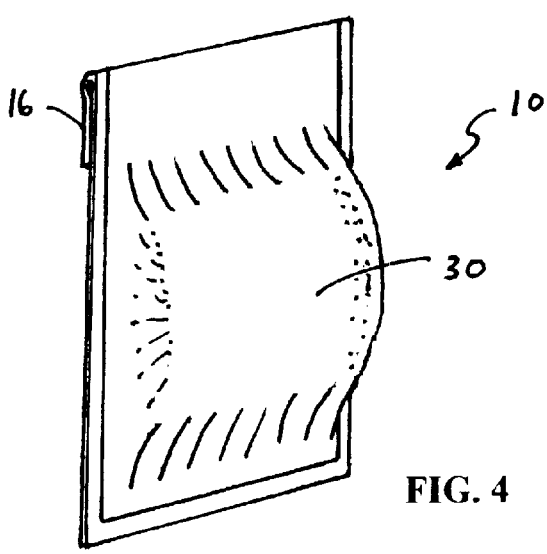
FIG. 4 is a back perspective view of the pouch style package of FIG. 1, showing a bulge formation in accordance with the present invention.

FIGS. 1, 2 and 4 illustrate an easy opening pouch style sealed containment and dispensing package 10 for flowable products according to the present invention. The package 10 includes at least two walls 20 sealed together about their periphery at edge seals 15, thereby forming an interior product containment region of the package 10. Package 10 includes an aperture forming means 40 and a flap portion 16. The specifics of the aperture forming means 40 and the flap portion 16 are discussed in greater detail below.

Figure 3:
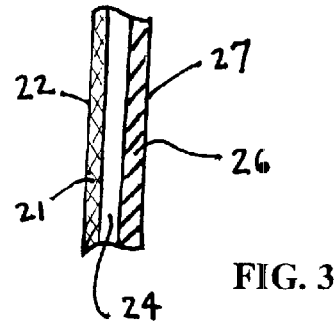
FIG. 3 is a cross-sectional view showing the laminated wall structure for a pouch style package in accordance with certain embodiments of the present invention.

As shown in FIG. 3, for example, the structure of package walls 20 are made of at least three layers of thin materials, i.e., an inner layer 21 having an inner wall face 22, an intermediate layer 24, and an outer layer 26 having an outer face 27. The layered structure of walls 20 is also depicted in FIG. 5. The specific number of layers employed to form the walls 20 of the package 10 may vary, for example, depending upon the desired use of the package 10, the desired barrier qualities of the package 10, and/or the chemistry of the products contained in the containment region of the package 10 and dispensed therefrom. Each of the layers 21, 24, and 26 is made from thin materials, which materials may be, but are not limited to, heat sealable plastic films, metal foils, oxygen barrier films, plastic moisture barrier films, adhesives, coextrudable plastics and high strength plastics, with a total thickness of about 0.003".

Notwithstanding the actual number of layers utilized to form the structure of the walls 20, it is necessary that the inner layers 21 and at least one of the outer layers 26 are heat sealable. The specific heat sealable inner layers 21 used are selected so as to have a sealing temperature significantly higher than the sealing temperature of the at least one heat sealable outer layer 26. A heat sealable outer layer 26 is used to form the flap layer, which is sealed to its own surface. On this basis, the outer face 27 of the portion of the outer layer 26 that forms the flap portion 16 can be easily heat sealed to the outer face 27 of the adjacent portion of the outer layer 26 at a temperature effectively lower than the sealing temperature of the inner layer 21. This sealing temperature differential will ensure that the opposing inner layers 21 of the package 10 will not become inadvertently sealed at wrong locations, thereby preserving the functionality of the package 10.

As noted above and shown in FIG. 1, the flap portion 16 of the package 10 is folded over to cover the pre-made aperture forming means 40. The pre-made aperture forming means 40 may take one of a number of forms, for example, the form of a fault line score pattern cut into, but not completely through, one of the walls 20, the form of a breakaway tip defined by a fault line score pattern, the form of a simple cut pattern cut through one of the walls 20, or the form of a pre-made hole punched or otherwise cut completely through one of the package walls 20. Examples of types of aperture forming means that may be used are described further and depicted in U.S. application Ser. No. 09/717,449, incorporated herein by reference.

Depending what aperture forming system is used, the flap portion 16 is either bonded by sealing or peelably sealed to or over the aperture forming means 40. For example, in the case of the breakaway tips and/or score patterns, the flap portion may be sealed by a hard seal directly to the breakaway portion within the score pattern. In the case of a pre-made hole or cut area, the flap portion is sealed over and beyond the aperture area, as shown by the seal area 50. The seal area 50 between the flap portion 16 and the at least one wall 20, as shown in FIG. 1, encompasses or overlaps the aperture forming means 40. In other cases the seal area may be directly within a score pattern that defines the aperture forming means 40.

As best shown in FIG. 5, an area of the outer layer 26 that is part of the flap member 16 is sealed to a sealing area of the same outer layer 26. Thus, at least two sections of the outer face 27, i.e., the same surface, are sealed together at or over the aperture forming means 40. The aperture forming means 40 is preferably disposed on, or in, one of the walls 20 and at a location either in the flap portion 16 or under the flap portion 16. Regardless of where the aperture forming means may be located, the flap portion 16 is sealed to cover the aperture forming means 40, and the aperture is created or exposed when the flap portion 16 is folded back, lifting it away from the outer face 27 of the package.

In certain embodiments of the invention, an intermediate layer 24 of the multilayer may be selected to deform at higher temperatures than those used to form the edge seals 15. Thus, the layer 24 will not lose strength at the sealing temperatures used to seal together the inner wall surfaces of the plastic film layer to create the edge seals 15. As mentioned above, this is advantageous because the film of the pouches must retain its tensile strength in order to be pulled through the machine that makes the pouches.

In the example shown in FIGS. 1, 2 and 4, at least one of the walls 20 of the package 10 is provided with a pre-formed bulging formation 30. It will be appreciated that both of the walls 20 may be provided with a pre-formed bulging formation. FIG. 6 shows an example of a foil pouch-type package with two pre-formed bulging formations 30 and 30'.

The pre-formed bulge formations 30 provide a significant increase in the containment volume of the pouch and also a consequent significant decrease in the materials per unit volume of the packages (for example, approximately 10 to 30 percent). They also tend to reduce or eliminate wrinkles about the walls 20 and the edge seals 15. FIG. 7 shows an old style prior art foil pouch with the typical wrinkles 60 inherent in the walls of such prior art pouches.

It will remain understood by those skilled in the art that the present invention, in its broader aspects, is not limited to the particular embodiments shown and described herein, and that variations may be made without departing from the principles of the invention and without sacrificing its chief advantages.

I claim:

1. A sealed containment and dispensing package for flowable products comprising:
    a pouch style package comprising at least three layers of thin materials of which one wall is comprised of at least two such layers of which one is an adhesive layer selected from a group of materials including heat sealable plastic films, metal foils, oxygen barrier films, plastic moisture barrier films, adhesives, coextrudable plastics and high strength plastics; and
    an aperture forming means disposed in one wall of said pouch style package, a flap portion of said pouch style package including a portion of said one wall being folded over and sealed to a sealing area of said one wall, thereby sealingly covering said aperture forming means;
    wherein when said flap portion is folded back and away, an outlet aperture is created in said pouch style package.

2. The sealed containment and dispensing package according to claim 1,
    wherein one of said at least three layers comprises an outer wall layer of heat sealable plastic film;
    wherein a first area of said outer wall layer comprises a contact face of said flap member covering said aperture forming means when folded over and sealed to said sealing area of said outer wall layer;
    wherein another of said at least three layers comprises an inner product contacting wall layer; and
    wherein said contact face of said flap member is sealed to said sealing area of said outer wall layer at a lower temperature than a sealing temperature for forming edge seals of said inner product contacting wall layer, said flap portion being sealed without further sealing said inner product contacting wall layer.

3. The sealed containment and dispensing package according to claim 2, wherein another one of said at least three layers comprises a high strength layer that will not lose a significant amount of strength at temperatures substantially higher than said sealing temperature for forming said edge seals, thereby giving the pouch style package the ability to maintain package tensile strength after being brought to said sealing temperature for forming said edge seals.

4. The sealed containment and dispensing package according to claim 1,
    wherein one of said at least three layers comprises an inner product contacting wall layer;
    wherein edges of said inner product contacting wall layer are sealed at a sealing temperature for forming edge seals;
    wherein another one of said at least three layers comprises a high strength layer that will not lose a significant amount of strength at temperatures substantially higher than said sealing temperature for forming said edge seals, thereby giving the pouch style package the ability to maintain package tensile strength after being brought to said sealing temperature for forming said edge seals.

5. A sealed containment and dispensing package for flowable products as recited in claim 1, wherein the aperture forming means comprises a pre-made cut pattern disposed in one wall of said pouch style package, and wherein the flap portion of said pouch style package is folded over and sealed to said sealing area of said one wall across said pre-made cut pattern, so that when said flap portion is folded back and away, an outlet aperture is created in said pouch style package.

6. The sealed containment and dispensing package according to claim 5,
    wherein one of said at least three layers comprises an outer wall layer of heat sealable plastic film;
    wherein a first area of said outer wall layer comprises a contact face of said flap member covering said aperture forming means when folded over and sealed to said sealing area of said outer wall layer;

wherein another of said at least three layers comprises an inner product contacting wall layer; and wherein said contact face of said flap member is sealed to said sealing area of said outer wall layer at a lower temperature than a sealing temperature for forming edge seals of said inner product contacting wall layer, said flap portion being sealed without further sealing said inner product contacting wall layer.

7. The sealed containment and dispensing package according to claim 5, wherein one of said at least three layers comprises an inner product contacting wall layer;

wherein edges of said inner product contacting wall layer are sealed at a sealing temperature for forming edge seals;

wherein another one of said at least three layers comprises a high strength layer that will not lose a significant amount of strength at temperatures substantially higher than said sealing temperature for forming said edge seals, thereby giving the pouch style package the ability to maintain package tensile strength after being brought to said sealing temperature for forming said edge seals.

8. A sealed containment and dispensing package for flowable products as recited in claim 1, wherein the aperture forming means comprises a pre-made fault line score pattern disposed in one wall of said pouch style package, and wherein the flap portion of said pouch style package is folded over and sealed to said sealing area of said one wall within said pre-made fault line score pattern, so that when said flap portion is folded back and away, an outlet aperture is formed in said pouch style package.

9. The sealed containment and dispensing package according to claim 8, wherein one of said at least three layers comprises an outer wall layer of heat sealable plastic film;

wherein a first area of said outer wall layer comprises a contact face of said flap member covering said aperture forming means when folded over and sealed to said sealing area of said outer wall layer;

wherein another of said at least three layers comprises an inner product contacting wall layer; and wherein said contact face of said flap member is sealed to said sealing area of said outer wall layer at a lower temperature than a sealing temperature for forming edge seals of said inner product contacting wall layer, said flap portion being sealed without further sealing said inner product contacting wall layer.

10. The sealed containment and dispensing package according to claim 8, wherein one of said at least three layers comprises an inner product contacting wall layer;

wherein edges of said inner product contacting wall layer are sealed at a sealing temperature for forming edge seals;

wherein another one of said at least three layers comprises a high strength layer that will not lose a significant amount of strength at temperatures substantially higher than said sealing temperature for forming said edge seals, thereby giving the pouch style package the ability to maintain package tensile strength after being brought to said sealing temperature for forming said edge seals.

11. The sealed containment and dispensing package according to claim 1, wherein said pouch style package has a pre-formed bulge in at least one wall to increase its product containment capability.

12. A sealed containment and dispensing package for flowable products comprising:

a pouch style package comprising at least three layers of thin materials of which one wall is comprised of at least two such layers of which one is an adhesive layer selected from a group of materials including heat sealable plastic films, metal foils, oxygen barrier films, plastic moisture barrier films, adhesives, coextrudable plastics and high strength plastics; and an aperture disposed in one wall of said pouch style package, a flap portion of said pouch style package including a portion of said one wall being folded over and sealed to a sealing area of said one wall, thereby sealingly covering said aperture;

wherein when said flap portion is folded back and away from said sealing area, said aperture is uncovered to allow dispensing of product from said pouch style package.

13. The sealed containment and dispensing package according to claim 12, wherein one of said at least three layers comprises an outer wall layer of heat sealable plastic film;

wherein a first area of said outer wall layer comprises a contact face of said flap member covering said aperture when folded over and sealed to said sealing area of said outer wall layer;

wherein another of said at least three layers comprises an inner product contacting wall layer; and wherein said contact face of said flap member is sealed to said sealing area of said outer wall layer at a lower temperature than a sealing temperature for forming edge seals of said inner product contacting wall layer, said flap portion being sealed without further sealing said inner product contacting wall layer.

14. The sealed containment and dispensing package according to claim 13, wherein another one of said at least three layers comprises a high strength layer that will not lose a significant amount of strength at temperatures substantially higher than said sealing temperature for forming said edge seals, thereby giving the pouch style package the ability to maintain package tensile strength after being brought to said sealing temperature for forming said edge seals.

15. The sealed containment and dispensing package according to claim 12, wherein one of said at least three layers comprises an inner product contacting wall layer;

wherein edges of said inner product contacting wall layer are sealed at a sealing temperature for forming edge seals;

wherein another one of said at least three layers comprises a high strength layer that will not lose a significant amount of strength at temperatures substantially higher than said sealing temperature for forming said edge seals, thereby giving the pouch style package the ability to maintain package tensile strength after being brought to said sealing temperature for forming said edge seals.

16. The sealed containment and dispensing package according to claim 12, wherein said pouch style package has a pre-formed bulge in at least one wall to increase its product containment capability.

17. A sealed containment and dispensing package for flowable products comprising a pouch style package as recited in claim 1, wherein said pouch style package has a pre-formed bulge in at least one wall to increase its product containment capability.

18. A sealed containment and dispensing package for flowable products comprising a pouch style package as recited in claim 1, having walls made of at least two thin materials one of which is aluminum foil, said package having a pre-formed bulge in at least one of said walls to increase its product containment capability.

19. A sealed containment and dispensing package for flowable products comprising a pouch style package as recited in claim 12, wherein said pouch style package has a pre-formed bulge in at least one wall to increase its product containment capability.

20. A sealed containment and dispensing package for flowable products comprising a pouch style package as recited in claim 12, having walls made of at least two thin materials one of which is aluminum foil, said package having a pre-formed bulge in at least one of said walls to increase its product containment capability.

* * * * *